United States Patent [19]
Wilks, Jr. et al.

[11] Patent Number: 5,185,640
[45] Date of Patent: Feb. 9, 1993

[54] MULTIFACETED PROBES FOR OPTICAL ANALYSIS

[75] Inventors: Paul A. Wilks, Jr., Darien; John P. Gaglione, Stratford, both of Conn.

[73] Assignee: Genral Analysis Corporation, South Norwalk, Conn.

[21] Appl. No.: 759,452

[22] Filed: Sep. 13, 1991

[51] Int. Cl.⁵ .......................................... G01N 21/35
[52] U.S. Cl. .................... 356/300; 250/339; 356/244
[58] Field of Search ............... 356/300, 244, 246, 346; 250/339

[56] References Cited

U.S. PATENT DOCUMENTS

| 4,835,389 | 5/1989 | Doyle | 356/436 |
| 5,096,294 | 3/1992 | Layzell et al. | 356/326 |

*Primary Examiner*—F. L. Evans
*Attorney, Agent, or Firm*—F. Eugene Davis, IV

[57] ABSTRACT

Multiple internal reflection, MIR, probes or internal reflection elements, IRE, use the principal of frustrated total internal reflection, FTIR, (also known as attenuated total reflection, ATR,) in infrared spectroscopy, spectrometers, and spectrophotometers. The probes have at least three facets at one end thereof in the form of a regular pyramid preferably at an apex angle of 45°. A modulated oscillating light source is located at one focus of a reflecting ellipsoidal optical element; the other focus is located at one of the facets. Detectors are similarly located with respect to each of the other facets at the focus of reflecting ellipsoidal element with other focus located at the associaed facet. One of the detectors is responsive to a reference wavelength of light, the other to a absorption wavelength of the component of the sample being analyzed. The signals from the detectors are demodulated synchronously with the oscillating light source and their demodulated signals subtracted to produce a signal proportional to the quantity of the component in the sample. A circular probe may have any number of facets. Probes of polygonal cross section may have a number of facets equal to the number of sides of the polygon with the base edges thereof congruent with the sides of the polygon. The probe is preferably coated with a reflecting layer at both ends thereof along the sides and at the bottom opposite to the facets so that only a predetermined portion is exposed to the sample.

22 Claims, 3 Drawing Sheets

MULTIFACETED PROBES FOR OPTICAL ANALYSIS

TECHNICAL FIELD

This invention related to Mulifaceted Probes for Optical Analysis utilizing internal reflection elements providing multiple internal reflection, frustrated total internal reflection, and attenuated total reflection. The invention further relates to infrared spectroscopy, spectrometers, and spectrophotometers and utilizes efficient reflecting ellipsoidal optical elements Probes, according to the invention, are particularly useful for dipping into liquids to analyze a component thereof, for example, carbon dioxide, $CO_2$, in carbonated beverages.

BACKGROUND ART

"Infrared Probes" consisting of an optically sensitive element that either projects into a process stream or into a beaker of fluid are well known Many of the probes now in use have an entry surface at the tip of the probe through which IR energy is directed at an angle that will give rise to internal reflection and an exit surface adjacent to the entry surface through which a portion of the energy that has been internally reflected down the rod and back exits to detectors. It is well known that because of the diverse paths that the various rays take, half of the energy exits from the exit face and half from the entrance face.

It is important in the operation of an infrared probe that the source is optically coupled to the entrance facet so that there is an efficient transfer of energy into the probe element and that the rays enter the facet at angles such that they will be internally reflected once within the probe element. A similar requirement for an efficient optical coupling exits to refocus emerging energy from the other facet onto the detector.

Means should be provided such that an infrared probe which projects into a beaker of fluid is always actively contacted by the same amount of fluid, otherwise absorption measurements will not be accurate It is highly desirable that such instruments not employ motors or other mechanical means, particularly if they are often to be carried from site to site.

DISCLOSURE OF THE INVENTION

This invention is an improvement over existing IR probes in that it makes use of three or more facets at the entrance end rather than two. In a three facet probe, one facet is used as the entrance face for IR Energy from the source. The other two facets become exit facets for two detectors one with a reference filter as a window and the other with an analytical wavelength filter as a window. As in the two faced probe, returning energy is distributed equally among the three facets so that one third of the energy reaches each detector The probe element itself may be cylindrical in cross section and it is easiest to fabricate and fasten in place. Other cross sections such as triangular or square may also be used, with the square cross section especially useful for a four facet system (one source facet plus three measurement facets).

Probes of polygonal cross section where the number of sides of the polygon is odd and equal to the number of facets may be desirable to insure equal distribution of energy exiting the facets.

A reflecting ellipsoidal optical element with the entrance facet located at one focus and a light source or detector located at the other provides for sufficient optical coupling to the probe. A small broad band light source, an electrical resistance element, may be caused to oscillate in intensity by modulating the power supplied thereto In this way, the output signals from the detectors may be synchronously demodulated therewith with the referenced signal subtracted from the analysis signals to provide a high signal to noise ratio.

In order to insure that a probe which is dipped into a beaker of fluid always comes in contact with a predetermined area of fluid, the probe is reflection coated along the top sides thereof, along the bottom, and along the bottom sides thereof to expose a predetermined area for interaction with the fluid.

The reflection coating at the bottom of the rod also reflects back those rays which might strike at an angle greater than the critical angle and thus be lost.

The probe is preferably coated with a material which is non-reactive with the sample being analyzed. Diamond coatings are particularly effective with organic, that is carbon containing, molecules. Such diamond coatings work well on probes comprising cubic zirconia utilized to analyze dissolved carbon dioxide in beverages.

OBJECTS OF THE INVENTION

It is therefore an object of the invention to provide multifaceted probes for optical analysis.

Another object of the invention is to provide such probes which may be conveniently utilized with at least a pair of detectors in order to achieve a high signal to noise ratio.

Other objects of the invention are to provide an optical system for efficiently transmitting energy into and out of the facets of the probe, to provide an instrument with no moving parts, and to provide an instrument with reproducible results with untrained operators, particularly in measuring fluid samples in a beaker.

Other objects of the invention will in part be obvious and will in part appear hereinafter.

The invention accordingly comprises an article of manufacture having a relationship between the various elements thereof and possessing features, properties, and relations of components and elements which are exemplified in the following disclosure. The scope of the invention is indicated in the claims.

BRIEF DESCRIPTION OF THE DRAWINGS

For a fuller understanding of the nature and objects of the invention, reference should be had to the following detailed description, taken in connection with the accompanying drawings, in which.

The same reference characters refer to the same elements throughout the several views of the drawings.

BEST MODE FOR CARRYING OUT THE INVENTION

Figure 1:
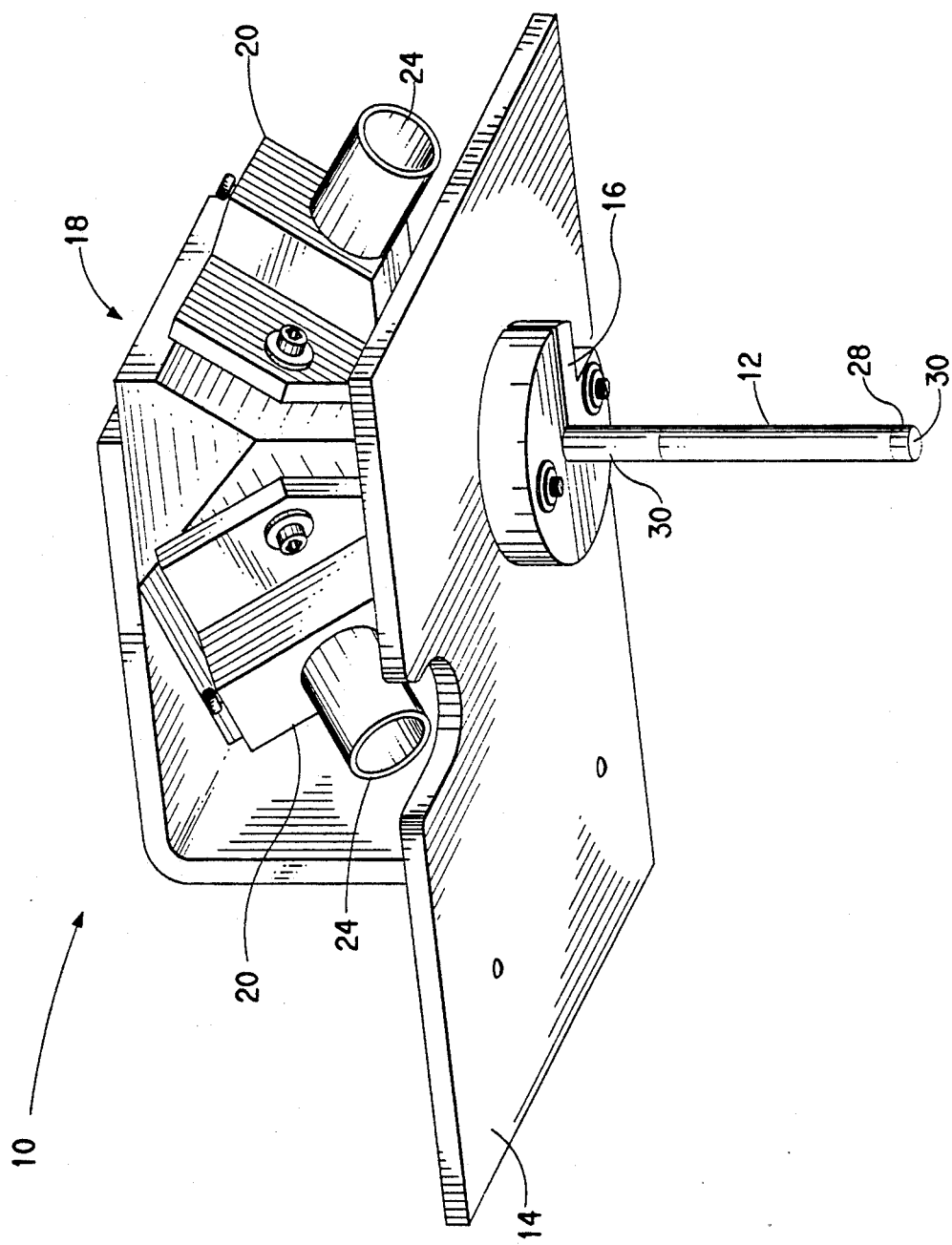
FIG. 1 is a perspective view of an assembled probe according to the invention.

Referring to FIG. 1, a probe assembly according to the invention is generally indicated at 10. It comprises the multi-faceted optical probe 12 which for carbon dioxide analysis may be of cubic zirconia, preferably coated with diamond so that bubbles of $CO_2$ gas will not adhere to the probe and affect the analysis.

The probe is mounted to mounting plate 14 by clamping element 16 which is screwed to mounting plate 14. The probe has three facets, see FIG. 3. An optical head, generally indicated at 18, comprises three identical assemblies 20, each providing a reflective ellipsoidal optical element 22, see FIG. 2 and a mounting tube 22 for a light source or detector.

Figure 2:
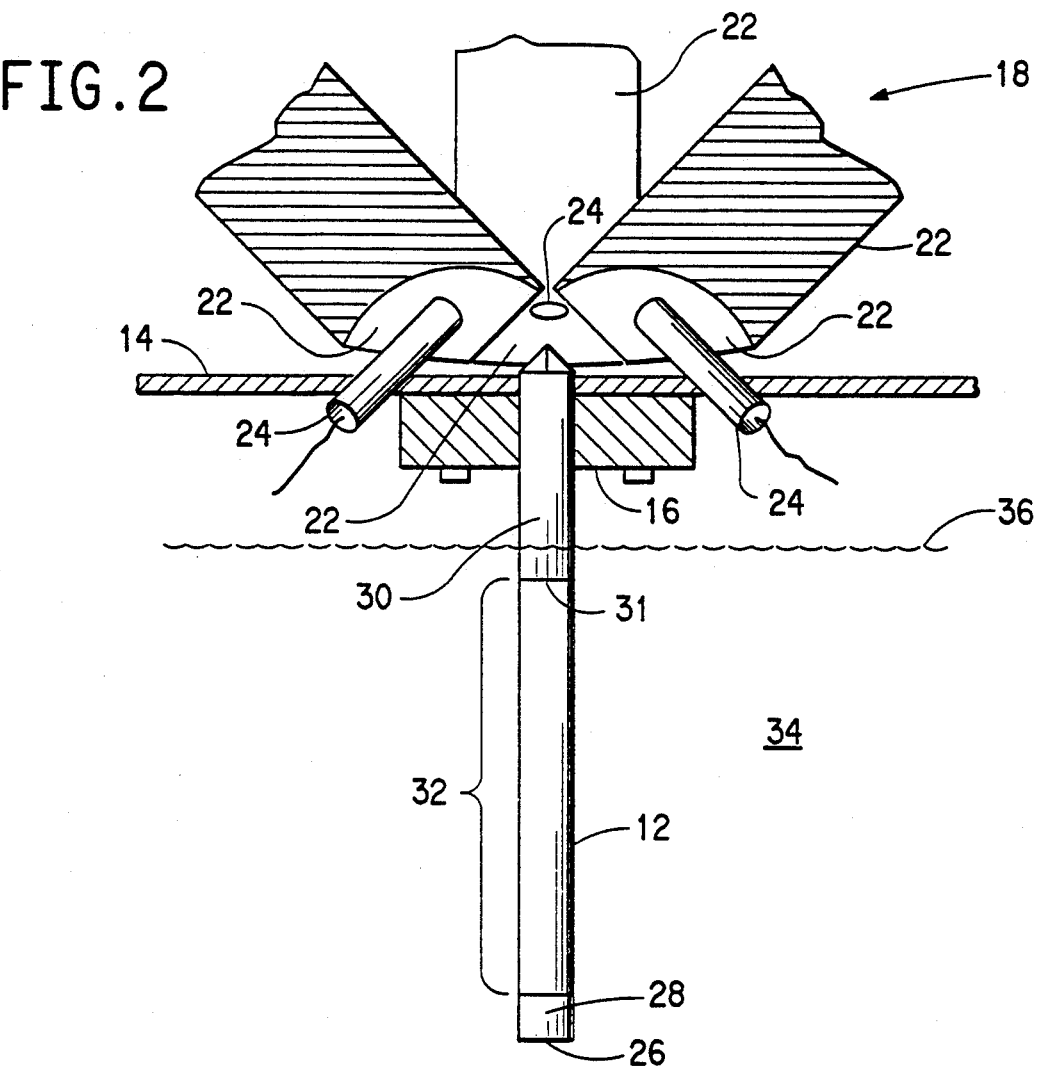
FIG. 2 is a diagrammatic side view of the probe of FIG. 1.

Now referring to FIG. 2, the multi-faceted probe 12 is preferably reflection coated at its non-faceted end 26 and along the adjacent sides 28. The bottom coating 26 reflects light which does not meet the bottom surface at the critical angle so that it is not lost. The side coating 28 and a similar side coating 30 at the top of the probe 12 defines a predetermined region 32 wherein the totally reflected rays interact with the surrounding sample 34. The operator insures that the probe 12 is inserted, such that the surface 36 of the sample 34 is above the bottom edge 31 of the coating 30, so that the entire predetermined region 32 is immersed within the sample 34.

Figure 3:
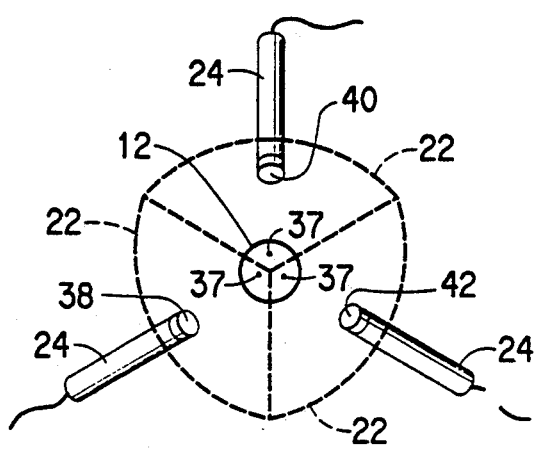
FIG. 3 is a diagrammatic top view thereof.

The ellipsoidal optical elements 22 are each cut from half of an ellipsoidal element which are easy to manufacture. Since there are three facets, the elements are sliced into a 120° pie shape so that they may be conveniently fitted together over the faceted end of the probe 12. One of the tubes 24 has a light source mounted therein, such that the light source is coincident with one focus of the ellipsoid; the other focus being coincident with the entrance facet such focus being indicated at 37. The top view of this arrangement is shown in FIG. 3 with the heated light source indicated at 38 and the filtered detectors 40 and 42 mounted adjacent to the other faces. Different mounting means for the source and detectors may be used, the important thing is that they be located at one focus of their respective ellipsoidal element.

Figure 4:
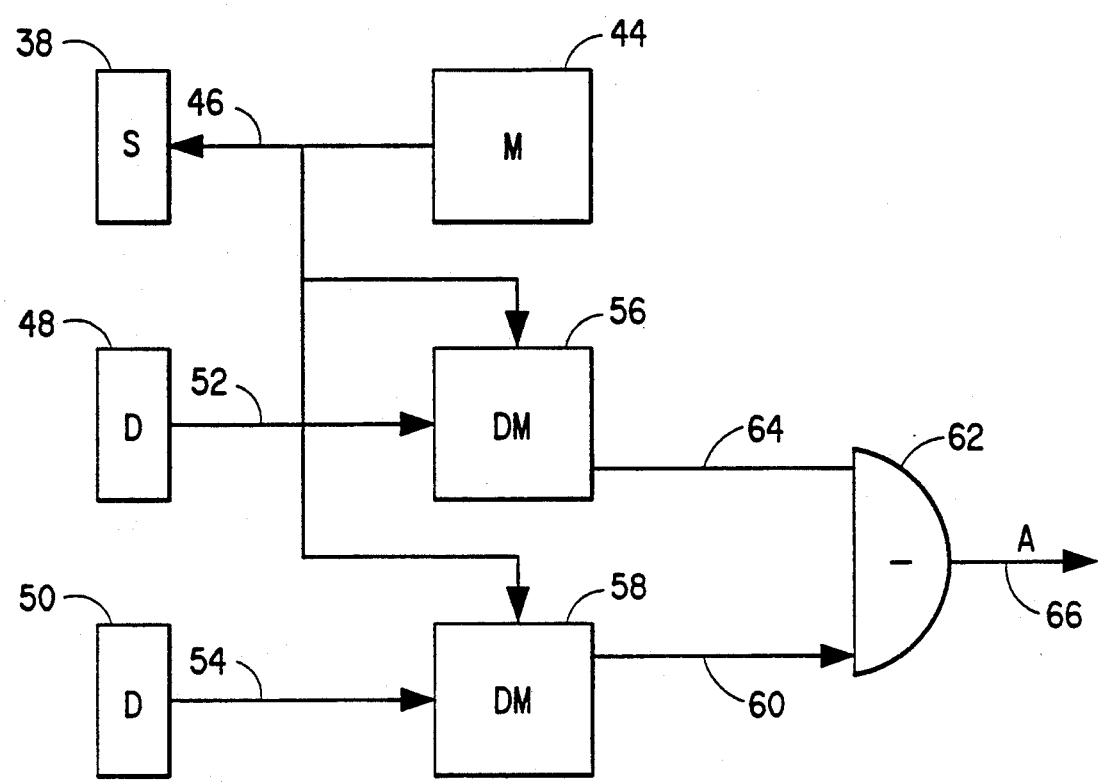
FIG. 4 is an electrical circuit diagram of an instrument using the probe of FIG. 1.

As shown in FIG. 4, at the focci of their respective ellipsoidal elements 22, the source 38 is preferably supplied from modulator 44 with a modulator signal on line 46 which causes the light source 38 to oscillate in intensity. One of the detectors has a filter mounted thereon at a characteristic absorption wavelength of the sample. The other reference detector 50 has a filter mounted thereon at a wavelength which is not absorbed by the sample. The signals therefrom are supplied on lines 52 and 54, respectively, to two demodulators 56 and 58. The signals from the reference detector 50 after demodulation is supplied on line 60 to an element 62 which subtracts it from the demodulated signal from the analyzing detector 48 on line 64. The resulting absorption signal is supplied on line 66 and indicates the amount of a particular molecule in the sample, for example, carbon dioxide in a beverage.

Figure 5:
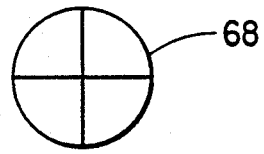
FIG. 5 is a diagrammatic view of a four-faceted probe of round cross section.

FIG. 5 shows a four-faceted probe of circular cross section 68 which may be used with two analyzing detectors.

Figure 6:
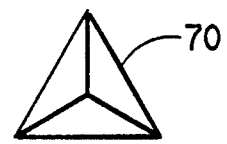
FIG. 6 is a top view of a three-faceted probe of triangular cross section.

FIG. 6 shows a triangular cross section probe 70 having three facets.

Figure 7:
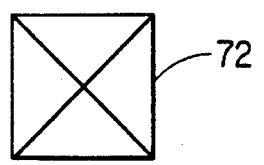
FIG. 7 is a .op view of a four-faceted square cross section probe.
Figure 8:
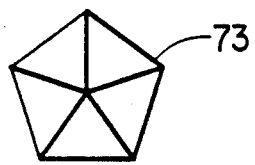
FIG. 8 is a top view of a five-faceted, five-sided polygonal probe.

FIG. 7 shows a square shaped probe 72 having four facets which may be conveniently used for measurements requiring two analyzing wavelengths and FIG. 8 shows a pentagonal cross section probe 73 having five facets which may be utilized to provide a reference detector and three analysis detectors at separate wavelengths.

Although we believe all of these probes will work, it can be seen that with the polygonal shaped detectors, those having an odd number of sides may disperse the light better, at least if they are short in length since light reflected from a face thereof will then be reflected from faces which are not parallel to the first face and thus scatter the light more readily than parallel faces which must rely upon the cone of acceptance of the light supplied.

It will thus be seen that the objects set forth above, among those made apparent from the preceding description, are efficiently attained and, since certain changes may be made in the above articles or combination without departing from the scope of the invention, it is intended that all matter contained in the above description shall be interpreted as illustrative and not in a limiting sense.

It is also to be understood that the following claims are intended to cover all of the generic and specific features of the invention herein described, and all statements of the scope thereof which, as a matter of language, might be said to fall therebetween.

Having described our invention, what we claim and desire to secure by Letters Patent is:

1. A probe for optical analysis comprising an elongated rod having at least three facets at one end thereof for the passage of light into or out of said probe.

2. A probe as defined in claim 1 wherein said facets form a regular pyramid.

3. A probe as defined in claim 1 wherein the end of said probe opposite to said facets is coated with a reflecting layer.

4. A probe as defined in claim 3 wherein the sides of said probe are coated with a reflecting layer adjacent to said faceted end so that a predefined exposed portion thereof between said reflecting layers will contact a sample.

5. A probe as defined in claim 4 wherein the coating at said opposite end extends up the sides of said probe.

6. A probe as defined in claim 1 wherein the cross section of said probe is circular.

7. A probe as defined in claim 1 wherein the cross section of said probe is triangular.

8. A probe as defined in claim 1 wherein the cross section of said probe is square.

9. A probe as defined in claim 1 wherein the cross section of said probe is polygonal and the number of facets is equal to the number of sides of said probe cross section.

10. A probe as defined in claim 9 wherein said facets form a regular pyramid with the base edges thereof congruent with the sides of said probe cross section.

11. A probe as defined in claim 10 wherein the number of said sides is odd.

12. A probe as defined in claim 1 and a light transparent non-reactive coating on said rod.

13. A probe as defined in claim 12 wherein said coating is non-reactive with carbon compounds.

14. A probe as defined in claim 12 wherein said coating is diamond.

15. A probe as defined in claim 1 and a reflecting ellipsoidal optical element associated with at least one of said facets having one of its foci at said facet and a light source at the other of said foci.

16. A probe as defined in claim 1 and a reflecting ellipsoidal optical element associated with at least one of said facets with one of its foci at said facet and a light detector at the other of said foci.

17. A probe as defined in claim 16 wherein there are two of said reflecting ellipsoidal optical elements each associated with a different one of said facets and with one of a pair of light detectors.

18. A probe as defined in claim 17 wherein said detectors respond to different wavelengths of light.

19. A probe as defined in claim 18 further comprising a modulated light source for directing light into one of said facets through a reflecting ellipsoidal optical element and means for demodulating signals received from said detectors and then subtracting the demodulated signals to provide a measurement signal.

20. A probe for optical analysis comprising an elongated rod having at least two facets at one end thereof for the passage of light therethrough and a pair of reflecting ellipsoidal optical elements each having one of its foci at a respective one of said facets for guiding the light that passes through said respective facet.

21. A probe as defined in claim 20 and a pair of light detectors each located at a respective one of the other foci of said reflecting ellipsoidal optical elements.

22. A probe as defined in claim 20 and a light detector located at the other foci of one of said ellipsoidal optical elements and a light source located at the other foci of the other of said ellipsoidal optical elements.

* * * * *